(12) United States Patent
Chung et al.

(10) Patent No.: US 9,964,436 B1
(45) Date of Patent: May 8, 2018

(54) IMAGE CAPTURING APPARATUS

(71) Applicant: Gingy Technology Inc., Hsinchu (TW)

(72) Inventors: Chuck Chung, Hsinchu (TW);
Jen-Chieh Wu, Hsinchu (TW)

(73) Assignee: Gingy Technology Inc., Hsinchu (TW)

( * ) Notice: Subject to any disclaimer, the term of this patent is extended or adjusted under 35 U.S.C. 154(b) by 0 days. days.

(21) Appl. No.: 15/826,711

(22) Filed: Nov. 30, 2017

Related U.S. Application Data

(63) Continuation-in-part of application No. 15/239,842, filed on Aug. 18, 2016.
(Continued)

(30) Foreign Application Priority Data

Jul. 18, 2016 (TW) .............................. 105122567 A
Sep. 20, 2017 (CN) .......................... 2017 1 0852899

(51) Int. Cl.
| | |
|---|---|
| G01J 1/04 | (2006.01) |
| F21K 9/60 | (2016.01) |
| G02B 7/36 | (2006.01) |
| H03K 17/94 | (2006.01) |
| G02B 13/14 | (2006.01) |
| G01S 17/02 | (2006.01) |
| G06K 9/00 | (2006.01) |
| G03B 9/06 | (2006.01) |

(52) U.S. Cl.
CPC ............. G01J 1/0411 (2013.01); F21K 9/60 (2016.08); G01S 17/026 (2013.01); G02B 7/36 (2013.01); G02B 13/14 (2013.01); H03K 17/941 (2013.01); G03B 9/06 (2013.01); G06K 9/00248 (2013.01)

(58) Field of Classification Search
CPC ............. G06K 9/0004; G06K 9/00053; G06K 2009/0006; G02B 27/30; G01J 1/0411
See application file for complete search history.

(56) References Cited

U.S. PATENT DOCUMENTS

| | | | |
|---|---|---|---|
| 2016/0132712 A1* | 5/2016 | Yang .................... | G06K 9/0002 348/77 |
| 2016/0224816 A1* | 8/2016 | Smith .................... | G02B 27/58 |

(Continued)

*Primary Examiner* — Michael Pervan
(74) *Attorney, Agent, or Firm* — JCIPRNET

(57) ABSTRACT

An image capturing apparatus including a cover plate, a light source, a sensor, and a collimator is provided. The light source and the sensor are located on the same side of the cover plate. The collimator is disposed between the cover plate and the sensor, and the collimator includes collimating elements overlapping with each other. Each collimating element includes a transparent substrate and a light absorbing layer disposed on the transparent substrate. The light absorbing layer includes a plurality of light passing openings. The light passing openings expose sensing areas of the sensor. Spacing between the light passing openings is S. A width of each light passing opening is W, and W<S. A transparent substrate thickness of a first collimating element in the collimating elements is T1. A transparent substrate thickness of a second collimating element in the collimating elements is T2. The image capturing apparatus satisfies:

$$0.3 \times \frac{W}{S} \times T1 \leq T2 \leq T1.$$

20 Claims, 5 Drawing Sheets

Related U.S. Application Data

(60) Provisional application No. 62/266,002, filed on Dec. 11, 2015, provisional application No. 62/533,632, filed on Jul. 17, 2017.

(56) References Cited

U.S. PATENT DOCUMENTS

2017/0220844 A1\* 8/2017 Jones .................... G06F 3/0416
2017/0270342 A1\* 9/2017 He ........................ G06F 3/0412

\* cited by examiner

IMAGE CAPTURING APPARATUS

CROSS-REFERENCE TO RELATED APPLICATION

This application is a continuation-in-part application of and claims the priority benefit of a prior application Ser. No. 15/239,842, filed on Aug. 18, 2016, now pending, which claims the priority benefits of U.S. provisional application Ser. No. 62/266,002, filed on Dec. 11, 2015, and Taiwan application serial no. 105122567, filed on Jul. 18, 2016. This application also claims the priority benefits of U.S. provisional application Ser. No. 62/533,632, filed on Jul. 17, 2017 and China application serial no. 201710852899.3, filed on Sep. 20, 2017. The entirety of each of the above-mentioned patent applications is hereby incorporated by reference herein and made a part of this specification.

BACKGROUND OF THE INVENTION

1. Field of the Invention

The invention relates to an optoelectronic apparatus and particularly relates to an image capturing apparatus.

2. Description of Related Art

The type of biometrics includes identification of faces, voices, iris, retina patterns, veins, palm prints and fingerprints. According to different detection methods, an identification apparatus for biological characteristics may be categorized into optical, capacitive, ultrasonic and thermal types. In general, an optical identification apparatus for biological characteristics includes a light source, a light guide element and a sensor. Light beams emitted by the light source radiates on an object to be identified that is pressed on the light guide element. The sensor receives the light beams reflected by the object to be identified to identify the biological characteristics. During the process of capturing images by the sensor, the light beams reflected by the fingerprints tend to be transmitted to the sensor in a disorganized manner, leading to the captured images of poor quality and influencing the result of identification. Despite some technologies aimed at improving the quality of the captured images, it is still difficult to address the problem of crosstalk effectively through advances in the current technology.

SUMMARY OF THE INVENTION

The invention provides an image capturing apparatus having a good identification capability.

The image capturing apparatus includes a cover plate, a light source, a sensor and a collimator. The sensor is disposed next to the light source. The light source and the sensor are located on the same side of the cover plate. The collimator is disposed between the cover plate and the sensor and includes a plurality of collimating elements overlapping with each other. Each of the collimating elements includes a transparent substrate and a light absorbing layer disposed on the transparent substrate. The light absorbing layer includes a plurality of light passing openings. The light passing openings expose a plurality of sensing areas of the sensor. Spacing between the light passing openings is S. A width of each of the light passing openings is W, and W<S. A transparent substrate thickness of a first collimating element in the collimating elements is T1, a transparent substrate thickness of a second collimating element in the collimating elements is T2, and the image capturing apparatus satisfies:

$$0.3 \times \frac{W}{S} \times T1 \leq T2 \leq T1.$$

According to an embodiment of the invention, a plurality of indentations are formed on a surface of the transparent substrate, and the light absorbing layer is disposed in the indentations of the transparent substrate.

According to an embodiment of the invention, the image capturing apparatus satisfies:

$$0.3 \times \frac{W}{S} \times T1 \leq T2 \leq 0.9 \times \frac{W}{S} \times T1.$$

According to an embodiment of the invention, the image capturing apparatus satisfies:

$$0.9 \times \frac{W}{S} \times T1 \leq T2 \leq T1.$$

According to an embodiment of the invention, the first collimating element is disposed between the second collimating element and the sensor.

According to an embodiment of the invention, the second collimating element is disposed between the first collimating element and the sensor.

According to an embodiment of the invention, the second collimating element includes n transparent substrates overlapping with each other, a thickness of each of the n transparent substrates is less than T1, and a total thickness of the n transparent substrates is T2.

According to an embodiment of the invention, the image capturing apparatus further includes a display panel that is disposed between the cover plate and the collimator.

According to an embodiment of the invention, the image capturing apparatus further includes a band-pass filter layer that is disposed between the display panel and the sensor, and a light emitting spectrum of the light source falls within a transmission spectrum of the band-pass filter layer.

According to an embodiment of the invention, the display panel is an organic light emitting diode display panel.

According to an embodiment of the invention, the image capturing apparatus further includes an adhesion layer that is disposed between the n transparent substrates.

In view of the foregoing, for the image capturing apparatus according to the embodiments of the invention, the design of $$0.3 \times \frac{W}{S} \times T1 \leq T2 \leq T1$$

makes the large-angle light beams reflected several times between the collimating elements and absorbed by the light absorbing layer, addressing the problem of crosswalk effectively and allowing the image capturing apparatus to have a good identification capability.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
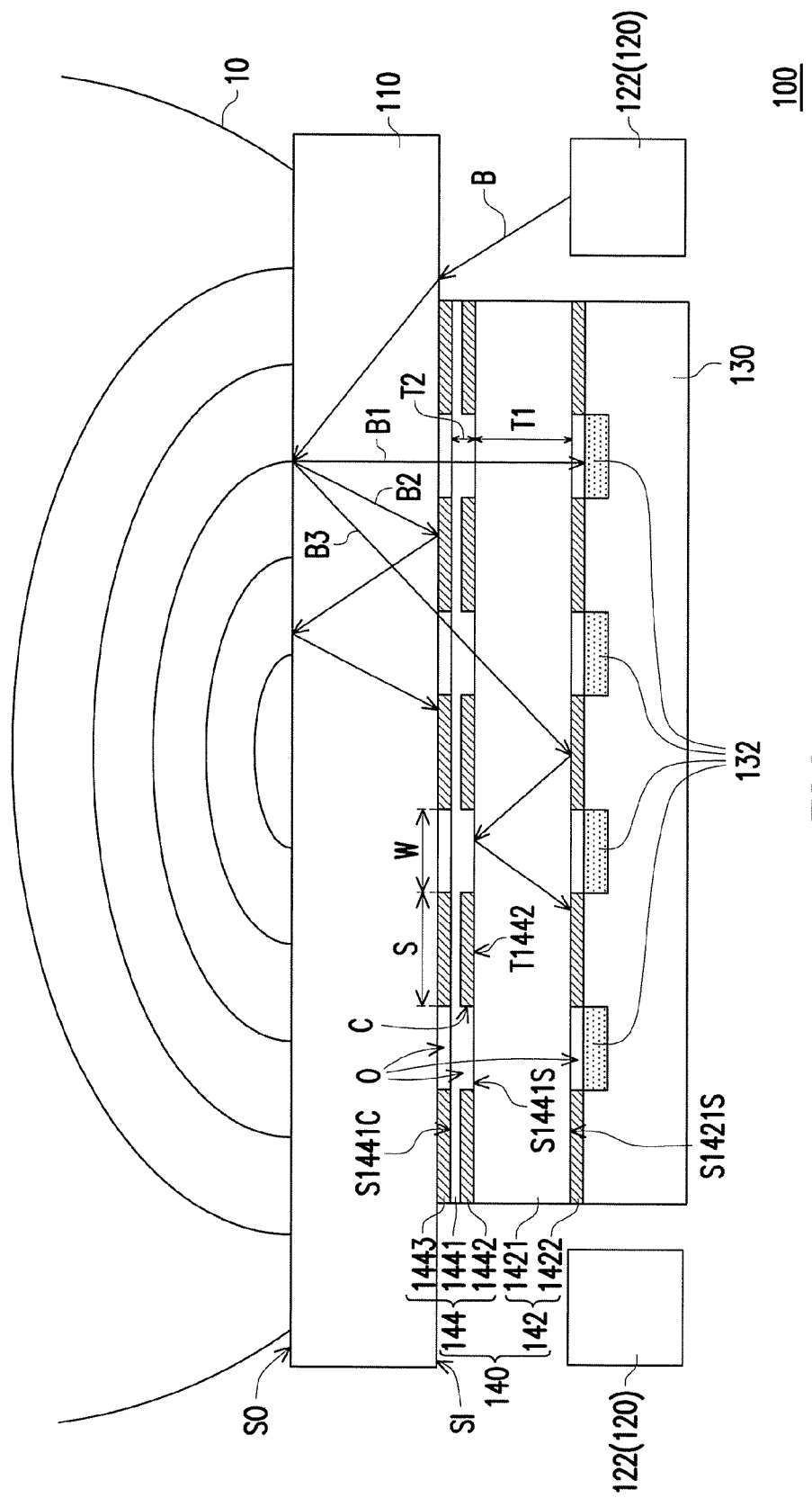
FIG. 1 is a sectional view of an image capturing apparatus according to a first embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Figure 2:
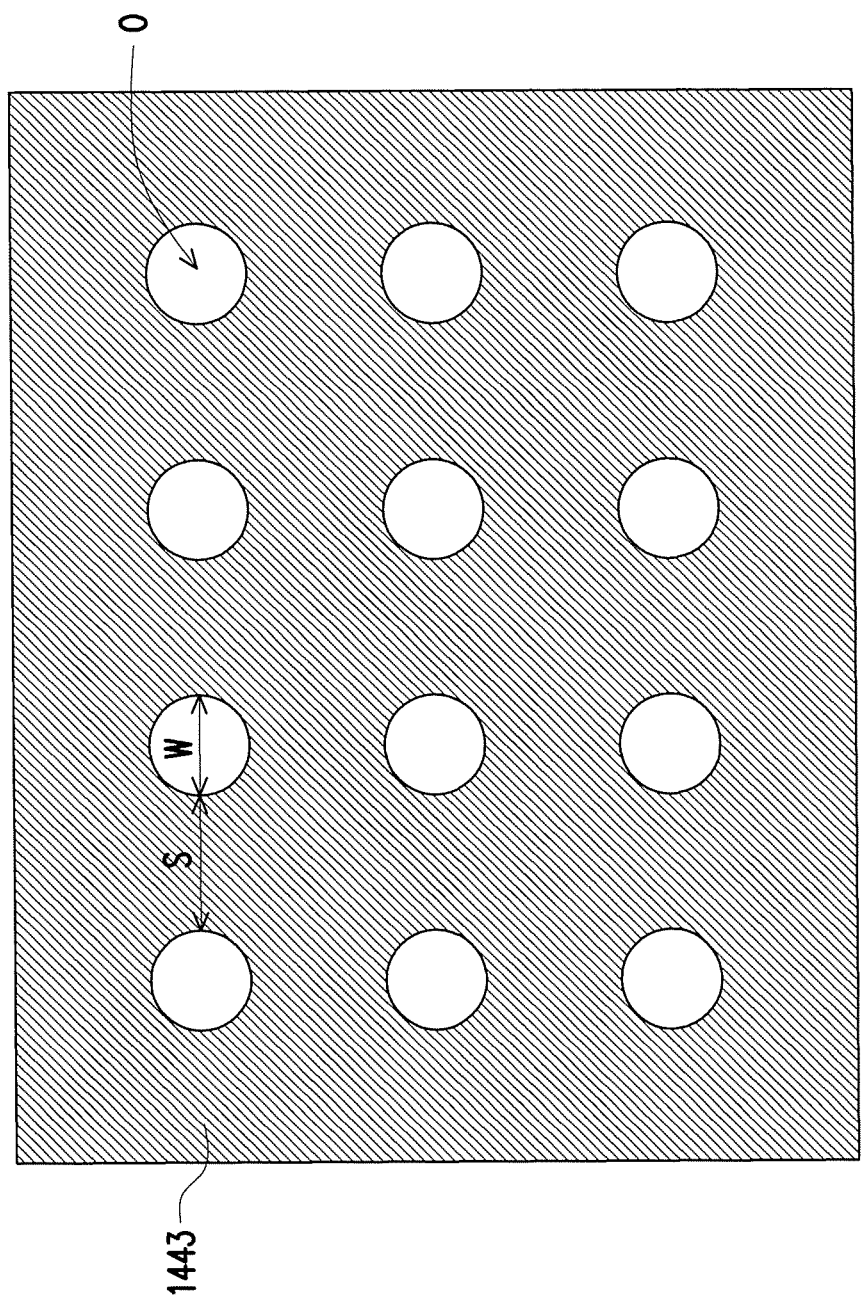
FIG. 2 is a top view of a collimator illustrated in FIG. 1.

FIG. 1 is a sectional view of an image capturing apparatus according to a first exemplary embodiment of the invention. FIG. 2 is a top view of a collimator illustrated in FIG. 1. Referring to FIGS. 1 and 2, an image capturing apparatus 100 according to the first exemplary embodiment of the invention is adapted to capture the biological characteristics of an object to be identified 10. For example, the object to be identified 10 is a finger, and biological characteristics are fingerprints or veins, but the object to be identified 10 and the biological characteristics are not limited thereto. In one exemplary embodiment of the invention, the object to be identified 10 may be a palm, and the biological characteristics may be palm prints.

The image capturing apparatus 100 includes a cover plate 110, a light source 120, a sensor 130 and a collimator 140. The sensor 130 is disposed next to the light source 120. The light source 120 and the sensor 130 are on the same side of the cover plate 110. The collimator 140 is disposed between the cover plate 110 and the sensor 130 and may be fixed between the cover plate 110 and the sensor 130 through an adhesion layer (not illustrated) or a fixing mechanism (not illustrated).

The cover plate 110 is adapted to protect elements disposed below, and the cover plate 110 may be a glass substrate or a plastic substrate. The glass substrate may be chemically or physically strengthened or not strengthened at all. The plastic substrate may be made from polycarbonate (PC), polyethylene terephthalate (PET), polymethylmethacrylate (PMMA), or polyimide (PI) or the like, but is not limited thereto.

The cover plate 110 includes an inner surface SI and an outer surface SO that is opposite to the inner surface SI. The inner surface SI of the cover plate 110 is a surface of the cover plate 100 facing toward the sensor 130, and the outer surface SO of the cover plate 110 is a contact surface of the object to be identified 10. In other words, the object to be identified 10 contacts the outer surface SO of the cover plate 110 to identify the biological characteristics.

The light source 120 is adapted to provide a light beam B radiating the object to be identified 10. The light source 120 may include a plurality of light emitting elements 122. Each of the light emitting elements 122 emits the light beam B toward the object to be identified 10. The light emitting elements 122 may include a light emitting diode, a laser diode or a combination thereof. Besides, the light beam B may include visible light, invisible light or a combination thereof. Invisible light may be infrared light, but is not limited thereto.

The sensor 130 is adapted to receive a portion of the light beam B reflected by the object to be identified 10 (i.e. a light beam B1 with information on fingerprint patterns). The sensor 130 may include a charge coupled device (CCD), a complementary metal-oxide semiconductor (CMOS) or other suitable types of image detection elements.

In one exemplary embodiment of the invention, the sensor 130 may be integrated with a pulse-width modulation circuit. The pulse-width modulation circuit controls light emitting time of the light emitting elements 122 and image capturing time of the sensor 130, so that the light emitting time of the light emitting elements 122 is synchronized with image capturing time of the sensor 130 to achieve accurate control, but the exemplary embodiment is not limited thereto.

The collimator 140 is adapted to collimate the portion of the light beam B that is reflected by the object to be identified 10 and transmitted toward the sensor 130. The collimator 140 includes a plurality of collimating elements overlapping with each other. In the exemplary embodiment, the collimator 140 includes two collimating elements such as a first collimating element 142 and a second collimating element 144, and the first collimating element 142 is disposed between the second collimating element 144 and the sensor 130. However, for the collimator 140, the number of the collimating elements and the relative location relationship between the collimating elements may vary based on demand, and are not limited to what is illustrated in FIG. 1.

Each of the collimating elements includes a transparent substrate and a light absorbing layer disposed on the transparent substrate. For instance, the first collimating element 142 includes a transparent substrate 1421 and a light absorbing layer 1422 that is disposed on a surface S1421S of the transparent substrate 1421 facing toward the sensor 130 and located between the transparent substrate 1421 and the sensor 130. The second collimating element 144 includes a transparent substrate 1441, a light absorbing layer 1442 and a light absorbing layer 1443. The light absorbing layer 1442 is disposed on a surface S1441S of the transparent substrate 1441 facing toward the sensor 130 and located between the transparent substrate 1441 and the transparent substrate 1421, and the light absorbing layer 1443 is disposed on a surface S1441C of the transparent substrate 1441 facing toward the cover plate 110 and located between the cover plate 110 and the transparent substrate 1441.

For each of the collimating elements, the numbers of the transparent substrates and the light absorbing layers, the relative location relationship between the transparent substrate and the light absorbing layer and a method of forming the light absorbing layer can vary based on demand, but are not limited to what is illustrated in FIG. 1. A plurality of indentations C are forming on the surface S1441S of the transparent substrate 1441, and the light absorbing layer 1442 is disposed in the indentations C of the transparent substrate 1441, allowing an outer surface T1442 of the light absorbing layer 1442 to line up with a portion of the surface S1441S without the indentations C. The method of forming the light absorbing layer 1442 may include the following steps: Firstly, the indentations C are formed on the surface S1441S of the transparent substrate 1441; secondly, light absorbing materials are formed in the indentations C; and afterwards, the light absorbing layer 1442 is formed by curing the light absorbing materials. In one exemplary embodiment, the transparent substrate 1441 and the indentations C may be formed through mold casting with the formation of the indentations C omitted.

In each of the collimating elements, the transparent substrates (such as the transparent substrate 1421 and the transparent substrate 1441) provide bearing surfaces for the light absorbing layers (such as the light absorbing layer 1422, the light absorbing 1442 and the light absorbing layer 1443), and the transparent substrates may be glass substrates or plastic substrates. The light absorbing layers are configured to absorb large-angle light beams (such as a light beam B2 or a light beam B3) of the light beam B that are reflected by the object to be identified 10 to collimate the light beams transmitted to the sensor 130. The light absorbing layer exhibits high absorptance and low reflectance to reduce the proportion of the light beams that are transmitted to and reflected by the light absorbing layer and the frequency of the light beams reflected by the light absorbing layer, further effectively reducing the proportion of the large-angle light beams received by the sensor 130. The low reflectance means the reflectance is less than 10% in visible and infrared bands. For instance, the light absorbing layer may be made from ink with low reflectance, but is not limited thereto.

In addition, in order to allowed the portion of the light beam B that is reflected by the object to be identified 10 (such as the light beam B1) to be received by the sensor 130, the light absorbing layer includes a plurality of light passing openings O. The light passing openings O expose a plurality of sensing areas 132 of the sensor 130. Specifically, the light passing openings O of the light absorbing layer 1422, the light absorbing layer 1442 and the light absorbing layer 1443 are disposed relative to the sensing areas 132 of the sensor 130. The sensing areas 132 may be places where a plurality of charge coupled devices are located or a plurality of pixel areas of a complementary metal-oxide semiconductor.

Spacing between the light passing openings O is S. A width of each of the light passing openings O is W, and W<S. A transparent substrate thickness of the first collimating element 142 is T1, a transparent substrate thickness of the second collimating element 144 is T2, and the image capturing apparatus 100 satisfies:

$$0.3 \times \frac{W}{S} \times T1 \le T2 \le T1.$$

The transparent substrate thickness of the collimating element refers to a total thickness of all the transparent substrates in the collimating element. In the exemplary embodiment, the first collimating element 142 includes only one transparent substrate (i.e. the transparent substrate 1421), and the second collimating element 144 includes only one transparent substrate (i.e. the transparent substrate 1441). Therefore, the transparent substrate thickness T1 of the first collimating element 142 is a thickness of the transparent substrate 1421, and the transparent substrate thickness T2 of the second collimating element 144 is a thickness of the transparent substrate 1441.

Under the design of $$0.3 \times \frac{W}{S} \times T1 \le T2 \le T1,$$

the large-angle light beams (i.e. the light beam B2 and the light beam B3) are reflected several times between the collimating elements and absorbed by the light absorbing layer to effectively address the problem of crosstalk and enable the image capturing apparatus 100 to have a good identification capability. In one exemplary embodiment, if the image capturing apparatus 100 satisfies the condition $$0.3 \times \frac{W}{S} \times T1 \le T2 \le 0.9 \times \frac{W}{S} \times T1,$$

the proportion of the large-angle light beams received by the sensor 130 may be further reduced, and a signal-to-noise ratio increases effectively to help a back end recognize a signal and noise, and thus raise possibilities of successful identification. In another exemplary embodiment, if the image capturing apparatus 100 satisfies the condition $$0.9 \times \frac{W}{S} \times T1 \le T2 \le T1,$$

the signal-to-noise ratio may be close to 0.

Figure 3:
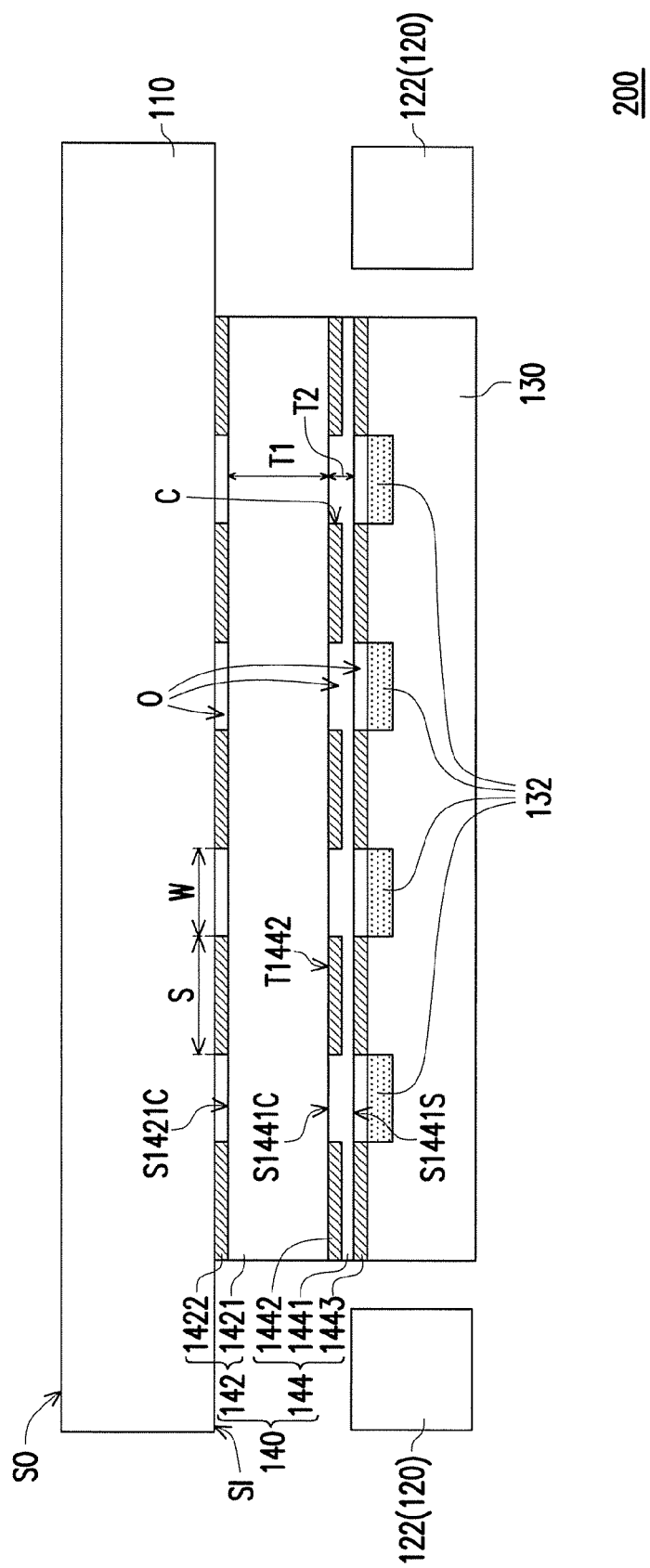
FIGS. 3 to 5 are sectional views of an image capturing apparatus according to second to fourth embodiments of the invention.
Figure 4:
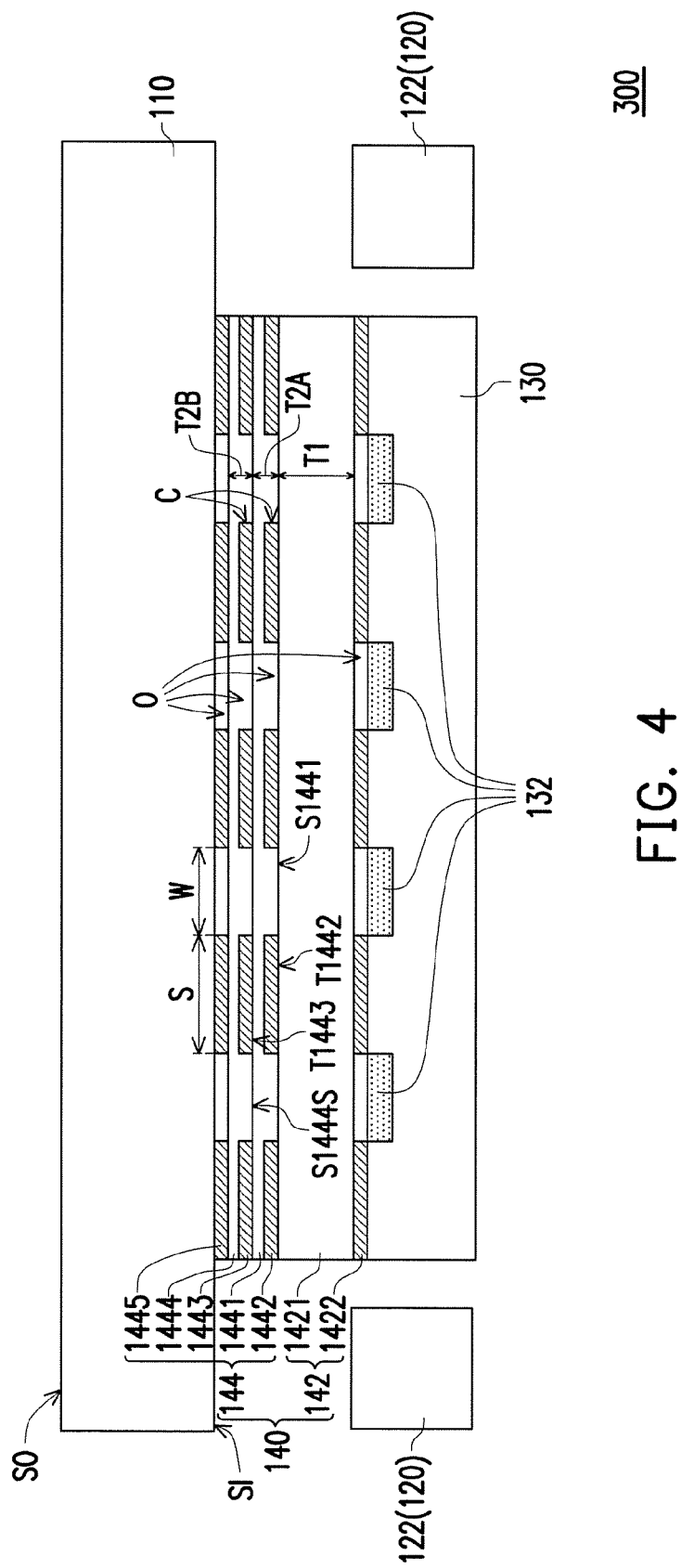
Figure 5:
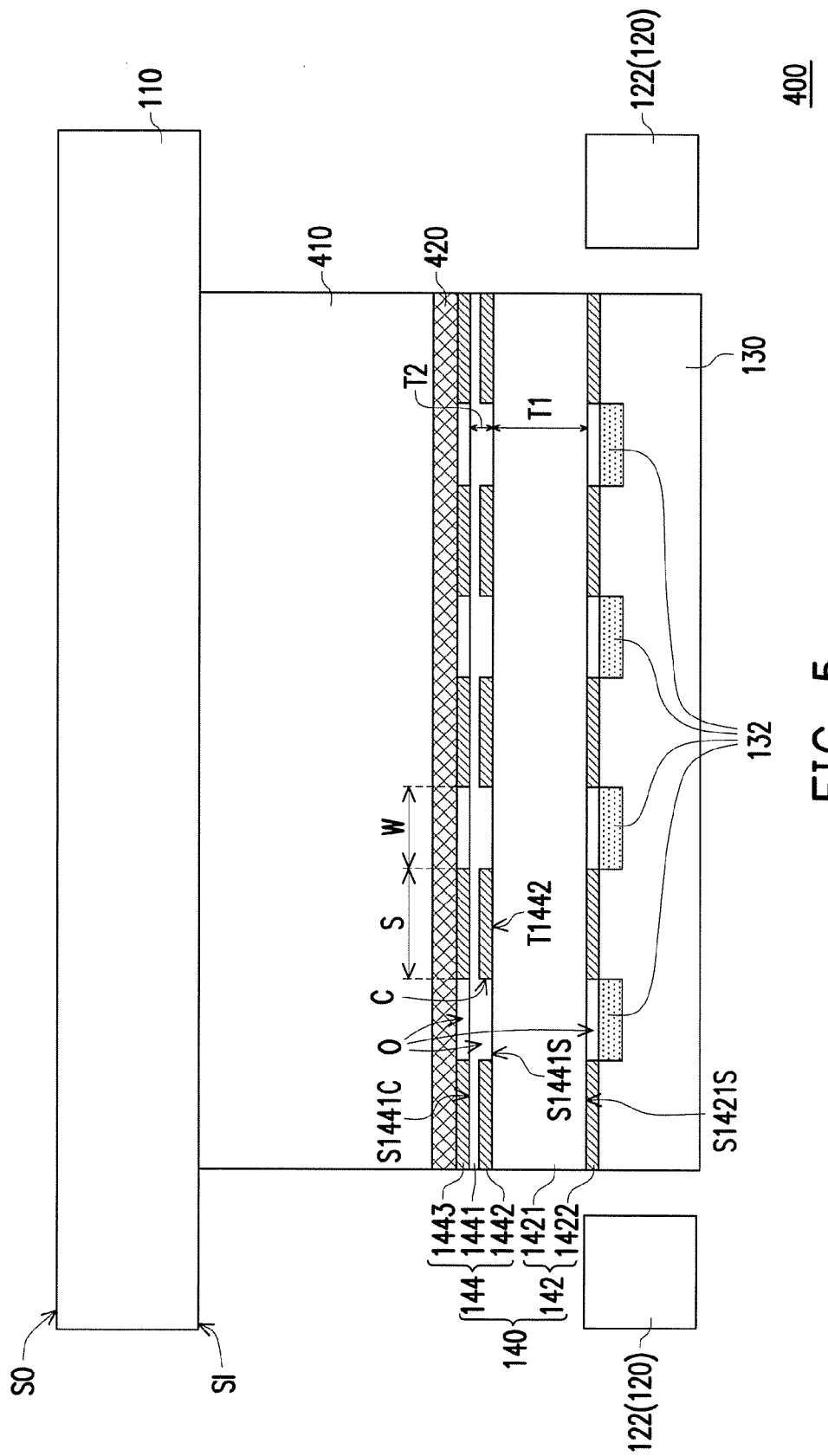

FIGS. 3 to 5 illustrate other embodiments of the image capturing apparatus where the same device is denoted by the same reference numeral. Redundant descriptions are not repeated here. FIGS. 3 to 5 are sectional views of the image capturing apparatus according to the second to fourth exemplary embodiments of the invention respectively.

Referring to FIG. 3, the main difference between an image capturing apparatus 200 according to the second exemplary embodiment of the invention and the image capturing apparatus 100 illustrated in FIG. 1 is presented below. In the image capturing apparatus 200, the second collimating element 144 is disposed between the first collimating element 142 and the sensor 130. Further, the light absorbing layer 1422 of the first collimating element 142 is disposed on a surface S1421C of the transparent substrate 1421 facing toward the cover plate 110 and located between the transparent substrate 1421 and the cover plate 110. The light absorbing layer 1442 of the second collimating element 144 is disposed on the surface S1441C of the transparent substrate 1441 facing toward the cover plate 110 and located between the transparent substrate 1441 and the transparent substrate 1421. The light absorbing layer 1443 of the second collimating element 144 is disposed on the surface S1441S of the transparent substrate 1441 facing toward the sensor 130 and located between the sensor 130 and the transparent substrate 1441. The indentations C are formed on the surface S1441C of the transparent substrate 1441, and the light absorbing layer 1442 is disposed in the indentations C of the transparent substrate 1441, allowing the outer surface T1442 of the light absorbing layer 1442 to line up with a portion of the surface S1441C that does not have the indentations C.

Referring to FIG. 4, the main difference between an image capturing apparatus 300 according to the third exemplary embodiment of the invention and the image capturing apparatus 100 illustrated in FIG. 1 is presented below. In the image capturing apparatus 300, in addition to the transparent substrate 1441, the light absorbing layer 1442 and the light absorbing layer 1443, the second collimating element 144 further includes a transparent substrate 1444 and a light absorbing layer 1445. In the exemplary embodiment, the transparent substrate 1444 is located between the transparent substrate 1441 and the cover plate 110, the light absorbing layer 1443 is located between the transparent substrate 1441 and the transparent substrate 1444, and the light absorbing layer 1443 and the light absorbing layer 1445 are located on opposite surfaces of the transparent substrate 1444 respectively. The indentations C are formed on a surface S1444S of the transparent substrate 1444 facing toward the sensor 130, and the light absorbing layer 1443 is disposed in the indentations C of the transparent substrate 1444, allowing an outer surface T1443 of the light absorbing layer 1443 to line up with a portion of the surface S1444S that does not have the indentations C.

A thickness T2A of the transparent substrate 1441 and a thickness T2B of the transparent substrate 1444 are less than T1, and a total thickness of the thickness T2A and the thickness T2B is T2. In other words, T2A+T2B=T2. In addition, the thickness T2A and the thickness T2B may be identical or different. In another exemplary embodiment, the second collimating element 144 may include two layers or more of the transparent substrates and three layers or more of the light absorbing layers. Likewise, the first collimating element 142 may include one layer or more of the transparent substrates and two layers or more of the light absorbing layers, and the transparent substrate thickness T1 of the first collimating element 142 is a total thickness of the one layer or more of the transparent substrates.

In addition, the second collimating element 144 of the image capturing apparatus 200 in FIG. 3 may also improve in the same way as described in the exemplary embodiment. Redundant descriptions are not repeated here.

Referring to FIG. 5, the main difference between an image capturing apparatus 400 according to a fourth exemplary embodiment of the invention and the image capturing apparatus 100 illustrated in FIG. 1 is presented below. The image capturing apparatus 400 further includes a display panel 410 and a band-pass filter layer 420. The display panel 410 is disposed between the cover plate 110 and the collimator 140 and adapted to provide images. For instance, the display panel 410 may be a thin film transistor liquid crystal display panel (TFT-LCD panel), a micro light emitting diode display panel (Micro LED display panel) or an organic light emitting diode display panel (OLED display panel), but is not limited thereto.

The band-pass filter layer 420 is disposed between the collimator 140 and the sensor 130 (not illustrated) or between the display panel 410 and the collimator 140 and is configured to let light beams from the light source 120 go through and filter out other light beams to prevent intervention caused by environmental light beams or light beams from the display panel 410 transmitted to the sensor 130, enhancing the identification capability of the image capturing apparatus 400. For instance, the band-pass filter layer 420 may be an infrared band-pass filter layer through which light beams with a wavelength of between 800 nm and 900 nm go through and which filters out other light beams without a wavelength of between 800 nm and 900 nm. Correspondingly, the light source 120 is an infrared light source with a wavelength of between 800 nm and 900 nm. In other exemplary embodiments, the band-pass filter layer 420 may be a band-pass filter layer 420 through which light beams with a wavelength of between 840 nm and 860 nm or between 890 nm and 990 nm go through, and the light source 120 may be an infrared light source with a wavelength between 840 nm and 860 nm or between 890 nm and 990 nm, but the invention is not limited thereto.

The image capturing apparatus 200 in FIG. 3 and the image capturing apparatus 300 in FIG. 4 may also further include the display panel 410 and the band-pass filter layer 420. Redundant descriptions are not repeated here.

In the above embodiment, the collimating elements may be fixed to each other through an adhesion layer (not illustrated) or a fixing mechanism (not illustrated). For instance, the adhesion layer may be formed between the transparent substrates of the collimating elements, so the collimating elements are firmly fixed to each other, but the invention is not limited thereto. The adhesion layer may be an optical clear adhesive (OCA) or a die attach film (DAF), but is not limited thereto.

In view of the foregoing, for the image capturing apparatus according to the embodiments of the invention, the design of $$0.3 \times \frac{W}{S} \times T1 \leq T2 \leq T1$$

makes the large-angle light beams reflected several times between the collimating elements and absorbed by the light absorbing layer to address the problem of crosswalk effectively and enable the image capturing apparatus to exhibit a good identification capability. In an exemplary embodiment, the image capturing apparatus may further include the display panel and thus provides a biological characteristic identification function and a display function. In another exemplary embodiment, the light source of the image capturing apparatus may be an infrared light source, and the image capturing apparatus may include the infrared band-pass filter layer to prevent intervention caused by the environmental light beams or the light beams from the display panel transmitted to the sensor, enhancing the identification ability of the electronic apparatus.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. A image capturing apparatus, comprising:
   a cover plate;
   a light source;
   a sensor, disposed next to the light source, wherein the light source and the sensor are located on the same side of the cover plate; and
   a collimator, disposed between the cover plate and the sensor and comprising a plurality of collimating elements overlapping with each other, wherein each of the collimating elements comprises a transparent substrate and a light absorbing layer disposed on the transparent substrate, the light absorbing layer comprises a plurality of light passing openings, the light passing openings expose a plurality of sensing areas of the sensor, spacing between the light passing openings is S, a width of each of the light passing openings is W, and W<S, and a transparent substrate thickness of a first collimating element in the collimating elements is T1, a transparent substrate thickness of a second collimat- ing element in the collimating elements is T2, and the image capturing apparatus satisfies:

$$0.3 \times \frac{W}{S} \times T1 \le T2 \le T1.$$

2. The image capturing apparatus of claim 1, wherein a plurality of indentations are formed on a surface of the transparent substrate, and the light absorbing layer is disposed in the indentations of the transparent substrate.

3. The image capturing apparatus of claim 1, wherein the image capturing apparatus satisfies:

$$0.3 \times \frac{W}{S} \times T1 \le T2 \le 0.9 \times \frac{W}{S} \times T1.$$

4. The image capturing apparatus of claim 1, wherein the image capturing apparatus satisfies:

$$0.9 \times \frac{W}{S} \times T1 \le T2 \le T1.$$

5. The image capturing apparatus of claim 1, wherein the first collimating element is disposed between the second collimating element and the sensor.

6. The image capturing apparatus of claim 1, wherein the second collimating element is disposed between the first collimating element and the sensor.

7. The image capturing apparatus of claim 1, wherein the second collimating element comprises n transparent substrates overlapping with each other, a thickness of each of the n transparent substrates is less than T1, and a total thickness of the n transparent substrates is T2.

8. The image capturing apparatus of claim 1 further comprising:
a display panel, disposed between the cover plate and the collimator.

9. The image capturing apparatus of claim 3 further comprising:
a display panel, disposed between the cover plate and the collimator.

10. The image capturing apparatus of claim 4 further comprising:
a display panel, disposed between the cover plate and the collimator.

11. The image capturing apparatus of claim 8 further comprising:
a band-pass filter layer, disposed between the display panel and the sensor, wherein a light emitting spectrum of the light source falls within a transmission spectrum of the band-pass filter layer.

12. The image capturing apparatus of claim 9 further comprising:
a band-pass filter layer, disposed between the display panel and the sensor, wherein a light emitting spectrum of the light source falls within a transmission spectrum of the band-pass filter layer.

13. The image capturing apparatus of claim 10 further comprising:
a band-pass filter layer, disposed between the display panel and the sensor, wherein a light emitting spectrum of the light source falls within a transmission spectrum of the band-pass filter layer.

14. The image capturing apparatus of claim 8, wherein the display panel is an organic light emitting diode display panel.

15. The image capturing apparatus of claim 7, further comprising:
an adhesion layer, disposed between the n transparent substrates.

16. The image capturing apparatus of claim 3, wherein the second collimating element comprises n transparent substrates overlapping with each other, a thickness of each of the n transparent substrates is less than T1, and a total thickness of the n transparent substrates is T2.

17. The image capturing apparatus of claim 4, wherein the second collimating element comprises n transparent substrates overlapping with each other, a thickness of each of the n transparent substrates is less than T1, and a total thickness of the n transparent substrates is T2.

18. The image capturing apparatus of claim 16, wherein the first collimating element is disposed between the second collimating element and the sensor.

19. The image capturing apparatus of claim 16, wherein the second collimating element is disposed between the first collimating element and the sensor.

20. The image capturing apparatus of claim 17, wherein the second collimating element is disposed between the first collimating element and the sensor.

* * * * *